United States Patent
Isoda

(10) Patent No.: US 9,980,908 B2
(45) Date of Patent: May 29, 2018

(54) LIPOSOME AND METHOD FOR PRODUCING LIPOSOME

(71) Applicant: Konica Minolta, Inc., Chiyoda-ku, Tokyo (JP)

(72) Inventor: Takeshi Isoda, Sayama (JP)

(73) Assignee: KONICA MINOLTA, INC., Chiyoda-Ku, Tokyo (JP)

( * ) Notice: Subject to any disclaimer, the term of this patent is extended or adjusted under 35 U.S.C. 154(b) by 275 days.

(21) Appl. No.: 14/598,603

(22) Filed: Jan. 16, 2015

(65) Prior Publication Data

US 2015/0125393 A1 May 7, 2015

Related U.S. Application Data

(63) Continuation of application No. 12/599,159, filed as application No. PCT/JP2008/058768 on May 13, 2008, now abandoned.

(30) Foreign Application Priority Data

May 14, 2007 (JP) ................................. 2007-127819

(51) Int. Cl.
| | | |
|---|---|---|
| A61K 9/127 | (2006.01) | |
| A61K 8/14 | (2006.01) | |
| A61K 8/41 | (2006.01) | |
| A61K 8/49 | (2006.01) | |
| A61K 8/63 | (2006.01) | |
| A61K 8/68 | (2006.01) | |
| A61K 31/7105 | (2006.01) | |
| A61K 31/713 | (2006.01) | |
| A61K 49/04 | (2006.01) | |
| A61Q 11/00 | (2006.01) | |
| A61Q 19/00 | (2006.01) | |
| B01J 13/02 | (2006.01) | |
| C12N 15/88 | (2006.01) | |
| A61K 31/7088 | (2006.01) | |
| A61K 49/00 | (2006.01) | |
| A23P 10/30 | (2016.01) | |
| A61K 47/62 | (2017.01) | |
| A61K 47/69 | (2017.01) | |

(52) U.S. Cl.
CPC ............ *A61K 9/1277* (2013.01); *A23P 10/30* (2016.08); *A61K 8/14* (2013.01); *A61K 8/416* (2013.01); *A61K 8/4986* (2013.01); *A61K 8/63* (2013.01); *A61K 8/68* (2013.01); *A61K 9/1271* (2013.01); *A61K 9/1272* (2013.01); *A61K 31/7088* (2013.01); *A61K 31/713* (2013.01); *A61K 31/7105* (2013.01); *A61K 47/62* (2017.08); *A61K 47/6911* (2017.08); *A61K 49/0002* (2013.01); *A61K 49/0466* (2013.01); *A61Q 11/00* (2013.01); *A61Q 19/00* (2013.01); *B01J 13/02* (2013.01); *C12N 15/88* (2013.01); *C12N 2810/85* (2013.01)

(58) Field of Classification Search
CPC ...................................................... A61K 9/127
See application file for complete search history.

(56) References Cited

U.S. PATENT DOCUMENTS

| | | |
|---|---|---|
| 5,204,112 A | 4/1993 | Hope et al. |
| 5,252,263 A | 10/1993 | Hope et al. |
| 5,326,484 A | 7/1994 | Nakashima et al. |
| 5,552,155 A | 9/1996 | Bailey et al. |
| 8,480,952 B2 * | 7/2013 | Nagaike ............... A61K 9/1277 264/4.1 |
| 2003/0185879 A1 | 10/2003 | Boulikas |
| 2004/0142025 A1 | 7/2004 | MacLachlan et al. |
| 2004/0197392 A1 | 10/2004 | Loekling et al. |
| 2005/0181038 A1 | 8/2005 | Haas et al. |
| 2006/0165770 A1 | 7/2006 | Zhang et al. |
| 2006/0198882 A1 | 9/2006 | Barenholz et al. |
| 2006/0220269 A1 | 10/2006 | Noritomi et al. |

(Continued)

FOREIGN PATENT DOCUMENTS

| | | |
|---|---|---|
| CA | 2491164 A1 | 1/2004 |
| CN | 1846844 A | 10/2006 |

(Continued)

OTHER PUBLICATIONS

English Translation of JP2006-317517, Sep. 2005.

(Continued)

*Primary Examiner* — Gollamudi Kishore
(74) *Attorney, Agent, or Firm* — Cantor Colburn LLP

(57) ABSTRACT

It is intended to provide a liposome preparation which is a liposome, has a lipid bilayer membrane composed of an inner membrane constituted by a lipid including one or more types of functional lipids (a lipid capable of chemically interacting with another compound such as a charged lipid, a polarizable lipid, a lipid-soluble lipid or a water-soluble lipid) and an outer membrane constituted by a lipid with or without including one or more types of functional lipids, and is characterized in that at least a condition that the amount of any one type of functional lipid contained in the inner membrane is larger than in the outer membrane is satisfied. The liposome preparation is suitable as a liposome for encapsulating a contrast agent (a neutral substance having a hydroxy group), siRNA (an anionic substance) having an anticancer activity or the like. Its encapsulation ratio of drug agents, dispersion stability, control release and the like have been improved.

14 Claims, No Drawings

(56) References Cited

U.S. PATENT DOCUMENTS

| | | | | |
|---|---|---|---|---|
| 2006/0239925 A1* | 10/2006 | Wada | ................... | A61K 9/1277 424/9.45 |
| 2008/0260648 A1* | 10/2008 | Takeyama | ............ | A61K 9/1694 424/9.32 |
| 2011/0206729 A1 | 8/2011 | Akiyoshi et al. | | |

FOREIGN PATENT DOCUMENTS

| | | | |
|---|---|---|---|
| JP | 5220382 A | | 8/1993 |
| JP | 2733729 B2 | | 3/1998 |
| JP | 2001139460 A | | 5/2001 |
| JP | 2003119120 A | | 4/2003 |
| JP | 2005162678 A | | 6/2005 |
| JP | 2005225822 | | 8/2005 |
| JP | 2005538967 A | | 12/2005 |
| JP | 2006272196 A | | 10/2006 |
| WO | 8707530 | | 12/1987 |
| WO | 9527478 | | 10/1995 |
| WO | 0134130 A1 | | 5/2001 |
| WO | 2004002453 A1 | | 1/2004 |
| WO | 2006080451 A1 | | 3/2006 |
| WO | 2006115155 A1 | | 11/2006 |
| WO | 2007032225 A1 | | 3/2007 |
| WO | 2008032225 A3 | | 3/2008 |
| WO | 2008121721 A2 | | 10/2008 |

OTHER PUBLICATIONS

Extended European Search Report for PCT/JP2008/058768, dated Nov. 25, 2013; 10 pages.
International Search Report for International Application No. PCT/JP2008/058768 dated Jun. 24, 2008 with English translation.
Notice of Reasons for Refusal for Japanese Patent Application No. 2009-514167, dated Mar. 12, 2013, with English translation.
Notice of Reasons for Rejections for Japanese Patent Application No. 2009-514167, dated Jan. 7, 2014, with English translation.
Sophie Pautot et al. "Production of Unilamellar Vesicles Using an Inverted Emulsion", Langmuir 2003, 19, 2870-2879.

* cited by examiner

LIPOSOME AND METHOD FOR PRODUCING LIPOSOME

The present application is a continuation application of U.S. patent application Ser. No. 12/599,159, filed on Nov. 6, 2009, the entire contents of which are incorporated herein by reference and priority to which is hereby claimed. Application Ser. No. 12/599,159 is the U.S. National stage of application No. PCT/JP2008/058768, filed on May 13, 2008. Priority under 35 U.S.C. § 119(a) and 35 U.S.C. § 365(b) is hereby claimed from Japanese Application No. 2007-127819, filed May 14, 2007 the disclosure of which is also incorporated herein by reference.

FIELD OF THE INVENTION

The present invention relates to a liposome which can be used as a drug carrier for pharmaceutical products, foods and cosmetics.

BACKGROUND OF THE INVENTION

A liposome is a closed vesicle having a lipid bimolecular membrane formed mainly of a phospholipid. Since a liposome has a similar structure and a similar function as a cell membrane, It will not stimulate easily an immunity system (low antigen) and it has a high safety level as a material. Moreover, it can retain a water-soluble medicine in an internal aqueous phase which is surrounded by a lipid bimolecular membrane, and it can retain a lipo-soluble medicine inside of the lipid bimolecular membrane. Therefore, it is possible to stably encapsulate medicinal properties which are originally easily deactivated. Active research and development have been made for application of a liposome in the field of pharmaceutical products, foods and cosmetics. In particular, it has been widely studied a medicine encapsulated liposome which is effectively applicable to a drug delivery system (DDS) (the content of studies are such as an adjustment of a particle size or a property of a lipid membrane of a liposome, and a targeting property to a specific cell) and a preparation method of a medicine encapsulated liposome.

In the present invention, the number of the lipid bimolecular membrane for constituting one liposome may be one, and it may be plural. That is, when the number of lipid bimolecular membrane is one, the bimolecular membrane concerned constitutes the outer shell of a liposome. On the other hand, when one liposome is composed of two or more lipid bimolecular membranes, any one of two or more lipid bimolecular membrane will constitute the outer shell of the liposome, and the remaining lipid bimolecular membranes will exist in the inside of the lipid bimolecular membrane which constitutes the outer shell.

The conventional liposome is manufactured by the way of forming lipid bimolecular membrane in one step, therefore, it is common that both inside and outside membrane of the liposome are made of the same constituting component (for example, refer to Patent document 1). Moreover, since the chemical property of the outer membrane participates in the dynamic state of the liposome in the living body, it may be employed a method to modify the outer membrane after usual preparation of the liposome. For example, in order to increase water solubility, a method may be employed in which the lipid of the outer membrane is combined with a polyoxyalkylene group (for example, refer to Non-patent document 1).

There has not been proposed a technique aiming at an improvement of a behavior in a living body such as an increased ratio of the encapsulated medicine or a controlled release (sustained-release) by making the constituting component of the inner membrane of the liposome which contacts with the medicine which should be sent different from an embodiment of the outer membrane. Or there has not been proposed a manufacturing method of a liposome having a different constituting component of an inner and an outer membrane.

Patent Document 1: Japanese Patent Application Publication open to public inspection (JP-A) 2005-162678
Non-patent Document 1: Biophys. J. 35,637-652, 1981

DISCLOSURE OF THE INVENTION

Problems to be Solved by the Invention

An object of the present invention is to provide a liposome drug formulation by which an encapsulated ratio of medicines, a dispersion stability and a controlled release have been improved.

Means to Solve the Problems

The present inventors have discovered the followings and have achieved the present invention: A liposome having a different constituting composition (an amount of a functional lipid) in the inner and in the outer membrane, i.e., a liposome containing a functional lipid which chemically interacts with a compound such as a medicine in a larger amount in the inner membrane than in the outer membrane, exhibits better properties of a encapsulate ratio of a medicine, a dispersion stability and a controlled release than other liposome containing the same amount of functional lipid in the inner and in the outer membrane. (The liposome of the present invention is also called as "Inner membrane functional liposome".); further, it is possible to produce the aforesaid liposome effectively by improving the conventionally known liposome production method (supercritical carbon dioxide method).

More specifically, the liposome of the present invention comprises a lipid bimolecular membrane composed of:
an inner membrane constituted with a lipid which contains one or more functional lipids; and
an outer membrane constituted with a lipid which contains or does not contain one or more functional lipids,
wherein an amount of at least one of the functional lipids contained in the inner membrane is larger than an amount of the one of the functional lipids contained in the outer membrane. The at least one of the functional lipids contained in the inner membrane is preferably a substance which chemically interacts with other compound. As the aforesaid "functional lipid", it is preferable to select one or more functional lipid from the group consisting of a charged lipid, a polarized lipid, a lipo-soluble lipid and a water-soluble lipid.

One of the preferred embodiments of the present invention is a liposome encapsulating a compound other than a solvent and constituting components of the membranes of the liposome. Examples of the aforesaid compound include: an anionic compound having a sequence of bases such as an siRNA which has an anticancer activity; and a neutral compound having a hydroxyl group such as a contrast medium.

The present invention provides a method for producing the aforesaid liposome. More specifically, one of the liposome production methods of the present invention is characterized by having the following steps (1) to (4):
(1) a first emulsion preparation step: mixing supercritical or semi-supercritical carbon dioxide, a water-soluble solvent (W1) and a mixed lipid component (F1) which forms an inner membrane of the liposome so as to prepare a W1/CO2 emulsion;
(2) a second emulsion preparation step: adding the W1/CO2 emulsion prepared in the step (1) to a mixture of a water-soluble solvent (W2) and a mixed lipid component (F2) which forms an outer membrane of the liposome with stirring so as to prepare a W1/CO2/W2 emulsion;
(3) eliminating the solvents contained in the W1/CO2/W2 emulsion prepared in the step (2) so as to prepare a suspension of the liposome comprising the inner membrane composed of F1 and the outer membrane composed of F2; and
(4) adding a compound to be encapsulated in the liposome to the suspension of the liposome prepared in the step (3), or to a water-soluble solvent in which a freeze-dried material of the suspension of the liposome prepared in the step (3) is re-dispersed,
  wherein an amount of at least one of the functional lipids contained in F1 of the step (1) is larger than an amount of the one of the functional lipids contained in F2 of the step (2).

Another one of the liposome production methods of the present invention is characterized by having the following steps (1) to (4):
(1) a first emulsion preparation step: mixing supercritical or semi-supercritical carbon dioxide, a water-soluble solvent (W1), a compound to be encapsulated in the liposome and a mixed lipid component (F1) which forms an inner membrane of the liposome so as to prepare a W1/CO2 emulsion;
(2) a second emulsion preparation step: adding the W1/CO2 emulsion prepared in the step (1) to a mixture of a water-soluble solvent (W2) and a mixed lipid component (F2) which forms an outer membrane of the liposome with stirring so as to prepare a W1/CO2/W2 emulsion; and
(3) eliminating the solvents contained in the W1/CO2/W2 emulsion prepared in the step (2) so as to prepare a suspension of the liposome comprising the inner membrane composed of F1 and the outer membrane composed of F2,
  wherein an amount of at least one of the functional lipids contained in F1 of the step (1) is larger than an amount of the one of the functional lipids contained in F2 of the step (2).

Effects of the Invention

The present invention has enabled to effectively produce an inner membrane functional liposome having excellent properties of an encapsulated ratio of medicines, a dispersion stability and a controlled release. It will greatly contribute the application of the medicine encapsulated liposome in the filed of DDS.

BEST MODE TO CARRY OUT THE PRESENT INVENTION

Constituting Component of Lipid Bimolecular Membrane (Liposome Membrane)
<Functional Lipid>
A "functional lipid" of the present invention indicates the following lipids among the lipids which can constitute an inner or an outer membrane of a liposome: a lipid which chemically carries out interaction with other compound (the other compound designates a compound other than a constituting component and a solvent which are used for producing a liposome); and a lipid having a functional property such as a bioactive effect. More specifically, examples of a functional lipid of the present invention include: a lipid which contributes to improve the encapsulation ratio or the retention efficiency of the medicine to be incorporated in the liposome and which is required to be incorporated mainly in the inner membrane of the liposome; or a lipid related to a behavior of a liposome in a living body (such as a targeting property) and required to be incorporated mainly in the outer membrane of the liposome.

In the present invention, it may be possible that the same functional lipid is contained both in an inner membrane and in an outer membrane of a liposome, or it may be possible that functional lipids each respectively contained in an inner membrane and in an outer membrane are different with each other. However, the liposome of the present invention satisfy the condition of: an amount of at least one of the functional lipids contained in an inner membrane is larger than an amount of the at least one of the functional lipids contained in an outer membrane. The detail will be described later. One of the preferred embodiments of the present invention is a liposome containing a specific functional lipid only in the inner membrane and not in the outer membrane, wherein the specific functional lipid can, for example, contribute to retain a specific compound to be incorporated in the liposome.

The aforesaid "interaction" is not specifically limited as long as the functional lipid contributes to retain "other compound" in a liposome. An interaction is a property capable of adhering, adsorbing or bonding to other compound. Examples of an interaction include: a hydrogen bonding between a hydroxyl group or an amino group, an ionic bonding, and other chemical interaction. More specifically, the compound to be incorporated in the liposome and the functional lipid constituting the liposome membrane are appropriately adjusted their formulations so as to achieve a suitable combination from the viewpoints of an interaction.

The aforesaid "interaction" may be an action which contributes to a stabilization of a liposome structure. It is well known that the stabilization of a liposome structure is made by strengthening the configuration of lipids thorough an interaction between lipids or by an interaction between a lipid and other compound. A liposome structure hardly broken can be formed thorough this effect.

As a functional lipid which can be used in the present invention, a charged lipid, a polarized lipid, a lipo-soluble lipid and a water-soluble lipid will be described. However, a functional lipid is not specifically limited to them. It may be possible to use other lipids which contribute to an increase of encapsulating ratio and retention efficiency into a liposome. It may be also possible to use other lipids which exhibit an interaction to increase stabilization, or which participate in the behavior of a liposome in a living body.
<Charged Lipid>
A charged lipid used in the present invention is a lipid having a positive or a negative charge under a biological pH condition and is capable of forming a bond with other compound via an electrostatic interaction.

Examples of a cationic lipid usable in the invention include 1,2-dioleoyloxy-3-(trimethylammonium)propane (DOTAP), N,N-dioctadecylamidoglycylspermine (DOGS), dimethyloctadecylammonium bromide (DDAB), N-[1-(2,3-dioleyloxyl)propyl]-N,N,N-trimethylammonium chloride (DOTMA), 2,3-dioleyloxy-N-[2(spermine-carboxamido)ethyl]-N,N-dimethyl-1-propaneaminiumtrifluoroacetate (DOSPA) and N-[1-(2,3-dimyristyloxy)propyl]-N,N-dimethyl-N-(2-hydroxyethyl)ammonium bromide (DMRIE), an ester of dipalmitoylphosphatidic acid (DPPA) with hydroxyethylenediamine, and an ester of distearoylphosphatidic acid (DSPA) and hydroxyethylenediamine.

A cholesterol derivative in which a cationic functional group is introduced is included in the aforesaid cationic lipid. One of a preferable example of a cationic cholesterol is: 3-□-[N—(N',N'-dimethylaminoethane)-carbamoyl]-cholesterol (DC-Chol) (refer to Biochem. Biophys. Res. Commun., 179, 1991, 280-285., and Chem. Pharm. Bull., 53, 2005, 871-880.)

Example of an anionic phospholipid include a glyceroline lipid which is negatively charged such as: phosphatidylserine, dipalmitoylphosphatidylserine (DPPS), distearoylphosphatidylserine (DSPS), phosphatidylglycerol, dipalmitoylphosphatidylglycerol (DPPG), distearoylphosphatidylglycerol (DSPG), dipalmitoyl-phosphatidylinositol (DPPI), distearoylphosphatidylinositol (DSPI), phosphatidic acid, dipalmitoylphosphatidic acid (DPPA) and distearoyl-phosphatidic acid (DSPA).

Examples of the above-described phospholipid may be: lecithin obtained from egg albumen, soybean, or other animals or plants; and a synthetic or a semi-synthetic product (such as a complete or partial hydrogenation product of a phospholipids, or a phospholipid derivative having polyetyleneglycol or aminoglycan in the molecule.)

<Polarized Lipid>

An aliphatic acid ester (R—CO—O—R') is one of preferable examples of a polarized lipid of the present invention. The ester bonding portion of an aliphatic acid ester will make an interaction with a compound (for example, with a neutral compound having a hydroxyl group and will be described later) encapsulated in a liposome on the surface of a liposome (on the surface facing the closed space of the liposome). It is supposed that, by this interaction, a chemical bonding such as a hydrogen bonding is formed to result in contributing to improvement of an encapsulating ratio of the compound.

An aliphatic acid residue "R" of the aforesaid aliphatic acid ester may be a saturated aliphatic acid residue or an unsaturated aliphatic acid residue. Preferably, it is a saturated aliphatic acid residue having a straight alkyl chain or a branched alkyl chain. The carbon number of the saturated aliphatic acid residue is preferably from 5 to 26, and more preferably it is from 5 to 24. When the carbon number is less than 5, a sufficient amount of the aliphatic acid ester will not be included in a lipid, which will result in lacking of stability by the effect of leaving from the membrane structure. On the other hand, when the carbon number is more than 28, the aliphatic acid ester will be decreased affinity to a living body.

Examples of an aliphatic acid which composes an aliphatic acid ester include: valerianic acid (valeric acid) (C5), caproic acid (C6), enanthic acid (C7), caprylic acid (C8), pelargonic acid (C9), capric acid (C10), lauric acid (C12), myristic acid (C14), pentadecyl acid (C15), palmitic acid (C16), margaric acid (C17), stearic acid (C18), arachidic acid (C20), behenic acid (C22) and lignoceric acid (C24).

"R'" in the aforesaid aliphatic acid ester is a straight or a branched alkyl group or alkenyl group having a carbon number of 1 to 4. Preferably it is an alkyl group (specifically preferable are a methyl group or an ethyl group). This alkyl group may be further substituted with the following groups: a halogen atom, an amino group, a hydroxyl group, a mercapto group, a nitro group, an alkoxy group, a carboxyl group, a carbamoyl group, a sulfonic acid group and a pyridyl group. An aliphatic acid ester having R' substituted with a hydrophilic group is amphiphilic, and it may produce a specific interaction with a compound to be encapsulated. Therefore, this ester is preferable.

In the present invention, it may be possible to use an aliphatic acid ester having a combination of R and R' as described above. Examples of a preferable aliphatic acid ester include: palmitic acid methyl ester, arachidic acid methyl ester, lignoceric acid methyl ester. Further, it may be possible to use the followings: a sugar ester (such as
an aliphatic acid sugar ester and an aliphatic acid sorbitan ester); and a polyoxyethylene aliphatic acid ester having a polyoxyethylene group.

<Lipo-Soluble Lipid>

Example of a lipo-soluble lipid is an ester derivative of cholesterol having a lipo-soluble ester portion. A liposome containing a lipo-soluble lipid in its membrane is supposed to have an increased uptake efficiency via oral administration or intestinal absorption.

<Water-Soluble Lipid>

Example of a water-soluble lipid is a compound which is introduced a polyoxyalkylene group (—(CH2CH2O)nH) in cholesterol. By introducing a polyoxyalkylene group in a lipid which forms a membrane, the surface of the liposome becomes hydrophilic. As a result, stability of a liposome will be improved (improvement in deterioration property and aggregation property), and it will produce an effect that the liposome will not be recognized as a foreign object.

<Other Lipid>

As a constituting component of the liposome of the present invention, a variety of known compounds can be used in addition to the aforesaid functional lipids. Examples of known compounds include: a neutral phospholipid, a glycolipid, a sterol derivative, a glycol derivative and an aliphatic amine.

Specific examples of a neutral phospholipid include: a neutral glyceroline lipid such as phosphatidylcholine, dipalmitoylphosphatidylcholine (DPPC), distearoyl-phosphatidylcholine (DSPC), dimyristoylphosphatidylcholine (DMPC), dioleylphosphatidylcholine (DOPC) and phosphatidylethanolamine; and a sphingophospholipid such as sphigomyelin.

Examples of a glycolipid include: a glycerolipid such as digalactosyldiglyceride and galactosyldiglyceride sulfuric acid ester; and sphingoglycolipids such as galactosylceramide, galactosylceramide sulfuric acid ester, lactosylceramide, ganglioside G7, ganglioside G6 and ganglioside G4.

Examples of a sterol derivative include: cholesterol, dihydrocholesterol, cholesterol ester, phytosterol, sitosterol, stigmasterol, campesterol, cholestanol, lanosterol; and further, a sterol derivative such as 1-O-sterolglucoside 1-O-sterolmaltoside and 1-O-sterolgalactoside. Among them, cholesterol is most preferable.

From the viewpoint of achieving stabilization of a liposome membrane, sterols are used preferably in a molar ratio of phospholipid (not including PEG-phospholipid)/sterols in the range of 100/60 to 100/90, and more preferably in the range of 100/70 to 100/85.

In addition, a cholesterol derivative becomes a cationic lipid or a lipo-soluble lipid by an introduction of a specific group in the ester portion of the molecule as describe above. A cholesterol derivative becomes an anchor to introduce a polyalkylene oxide and various functional substances can be efficiently fixed at the top of a polyoxyalkylene chain via a covalent bond (for example, refer to JP-A No. 09-003093.)

Examples of a glycol derivative include: ethylene glycol, diethylene glycol, triethylene glycol, propylene glycol, dipropylene glycol, trimethylene glycol and 1,4-butanediol. By using a glycol derivative, it is possible to improve a retention efficiency of a water-soluble medicine which should be encapsulated in a liposome. Glycols are used preferably in an amount of 0.01 to 20 weight % based on the total weight of the lipid, and more preferably 0.05 to 0.1 weight %.

Examples of an aliphatic amine are selected from primary and secondary amines which are allowed to be used by considering a pharmaceutical aspect and which have a straight or a branched alkyl group of carbon number of 2 to 22. Examples of such amines include: stearylamine, octylamine, oleylamine and linoleylamine. These aliphatic amines can be used for giving an electric charge to a liposome. When aliphatic amines are used, an amount of use is preferably 0.01 to 0.5 weight % based on the total weight of the lipid, and more preferably 0.05 to 0.1 weight %.

<Addition Amount of Functional Lipid>

An inner membrane functional liposome of the present invention is characterized by satisfying the condition of the following: an amount of one of the functional lipids contained in the inner membrane is larger than an amount of one of the functional lipids contained in the outer membrane.

The only requirement is that at least one of the functional lipids should satisfy the aforesaid condition. Other functional lipids may be contained in the inner membrane and in the outer membrane without satisfying the aforesaid condition. Further, it may be possible that a plurality of functional lipids each satisfy the aforesaid condition.

When a liposome satisfies the aforesaid condition with respect to a functional lipid which contributes to retention of a compound to be encapsulated in the liposome, the compound to be encapsulated is prevented from making interaction with a liposome surface (a surface adjacent to an external ambience) during the preparation. As a result, the liposome surface becomes so flat that the liposome is hardly aggregated and high dispersion stability can be obtained.

Here, "addition amount of functional lipid" indicates an absolute amount (mol number) of a functional lipid to be added as a raw material in the production of a liposome of the present invention, which will be described later. The only requirement is that the added amount of the aforesaid functional lipid in an inner membrane forming step is larger than the added amount of the aforesaid functional lipid in an outer membrane forming step. By considering the above-described effect, one of the preferred embodiments of the present invention is as follows: an embodiment of using a functional lipid which contributes to retention of a compound to be encapsulated in the liposome only in an inner membrane forming step, and producing a liposome containing the aforesaid functional lipid only in the inner membrane.

An amount of a functional lipid in an inner membrane and in an outer membrane can be adjusted in accordance with the application of the liposome, the degree of the purposed function and the kind of the functional lipids with taking into consideration of the publicly known knowledge. It is possible to adjust the amount of the specific functional lipid in the inner membrane and in the outer membrane to have a predetermined ratio via a production method which will be described later. For example, when a liposome having high dispersion stability is required to produce, it is preferable that a functional lipid which contributes to retention of a compound to be encapsulated in the liposome has a content ratio of "amount contained in the inner membrane/amount contained in the inner membrane" is in the range of from 100/1 to 100/50.

One of the embodiments of an inner membrane functional liposome of the present invention is made as follows: to make an inner membrane and an outer membrane composed of mainly dipalmitoylphosphatidylcholine (DPPC) and cholesterol, and to incorporate a charged lipid contributing to retention of a medicine only in the inner membrane, while to incorporate a water-soluble lipid relating to stabilizing of a liposome and to behavior of a liposome in a living body only in an outer membrane, and to make the amount of the aforesaid charged lipid to be larger than the amount of the aforesaid water-soluble lipid. The added amount of the functional lipids in the above-described embodiment of liposome is preferably as follows: DPPC/Cholesterol/functional lipid=about 10/2/1 in the inner membrane; and DPPC/Cholesterol/functional lipid=about 10/2/0.1 in the outer membrane.

Compound to be Encapsulated in Liposome

A variety of compounds can be effectively encapsulated (retained) in an inner membrane functional liposome of the present invention. Here, the above-described "compound to be encapsulated in liposome" is a compound appropriately selected in accordance with the applications of the liposome. It is a compound which can make a chemical interaction with a functional lipid which constitutes a liposome membrane. It is used in the production method that will be described later. It is a compound other than a constituting component of a liposome membrane and a solvent.

Representative examples of the above-described "compound to be encapsulated in liposome" are a variety of medicines (a variety of effective components to achieve a predetermined purpose) which are conventionally used in a liposome for medical use. For example, a water-soluble medicine which becomes a cation or an anion in a water solution is supposed to improve retention efficiency via an interaction with a charged lipid among the aforesaid functional lipids.

Compounds to be encapsulated in a liposome will be described with reference to "contrast medium" and "siRNA" which are appropriate medicines in the present invention. However, the target compounds of the present invention are not limited to these medicines. The other compounds which exhibit the same effect as these medicines with respect to an interaction with a functional lipid can be applied to the present invention.

In the present invention, a variety of conventionally known pharmaceutical adjuvants can be used in addition to the following medicines. Examples of a pharmaceutical adjuvant includes: a water-soluble amine buffer (preferably such as Trometamol); a pH buffer agent such as a carbonate salt buffer; a chelating agent (an edetic acid chelating agent such as EDTANa2-Ca); an antioxidant such as □-tocopherol, ascorbic acid; and other compounds such as an osmo-regulating agent, a stabilizer, a viscosity modifier, a preservative, an inorganic salt, further, a pharmacology activity substance such as a vasodilator and a freezing retarder.

<Contrast Medium>

Examples of an iodine compound which can be used in the present invention as an iodine contrast medium for X rays are nonionic iodine compound such as: iomeprol, iopamidol, iohexol, iopentol, iopromide, ioxilane, iosimide, iovensol, iotrolan, iodixanol, iodecimol, iotasul, metrizamide and 1,3-bis-[N-3,5-bis-(2,3-dihydroxypropylaminocarbonyl)-2,4,6-triiodophenyl]-N-hydroxyacetyl-amio]- propane. Among these compounds, preferred compounds are: iohexol, iomeprol, iopamidol, iotrolan and iodixanol, which exhibit high hydrophilicity and a low osmotic pressure even at relatively high concentration.

<siRNA>

Biopolymers (including oligomers) such as nucleic acids (DNA, RNA) and proteins will be negatively or positively charged depending on the condition of pH of a solvent. As a result, they can be bonded with the aforesaid functional molecule via an electrostatic force or via other interaction. In the present invention, it is possible to incorporate a biopolymer for a medical use into a liposome without specific limitation.

In recent yours, an siRNA (small interfering RNA) has been expected to be applied to gene therapy. And it is one of the preferable medicines to be encapsulated in a liposome. An example is an siRNA having an anticancer activity to restrain the activity of a gene which is important for multiplication of a cancer cell. Moreover, nucleic acids having a base sequence according to an application can be used. Examples of these nucleic acids include: a sense strand of DNA or RNA, an antisense strand, a plasmid, a vector and mRNA.

<Other Medicine>

In the present invention, various medicines can be effectively encapsulated in a liposome other than the aforesaid contrast media and siRNA. Examples of them include: antibacterial agent such as lysomycin, levofloxacin, streptomycin, rifampicin, amphotericin B, nystatin and midecamycin; substance in a living body such as interferon, erythropoietin, interleukin and porphiline; other water soluble vitamins; water-soluble non-electrolytic medicine such as ascorbic acid dipamitate, hesperidin, rutin, naringin and digoxin.

A Method for Producing a Liposome

The inner membrane functional liposome of the present invention is produced by methods such as a "microencapsulation method", a "membrane emulsion method", or a "supercritical carbon dioxide method" to be described later. The liposome of the present invention can be produced using a common apparatus and method under normal conditions (stirring condition, temperature condition, and pressurization condition) which are basically the same conditions as conventional ones for the microencapsulation method or the membrane emulsion method. However, the present invention is characterized in that with regard to the amount of at least 1 type of functional lipid, the added amount thereof in a first emulsion preparation step (inner membrane formation) is allowed to be larger than that in a second emulsion preparation step (outer membrane formation).

<Microencapsulation Method>

The microencapsulation method refers to a well-known method to produce a liposome (for example, refer to Japanese Patent Publication Open to Public Inspection No. 2001-139460) and the outline of its preparation steps is described below.

(1) First Emulsion Preparation Step: A water-soluble solvent (W1), an organic solvent (O), and a mixed lipid component (F1) which forms the inner membrane of a liposome are stirred to prepare a W1/O emulsion. The inner portion of a single membrane composed of F1 is a water phase (W1) and the outer portion thereof is an oil phase (O).

(2) Second Emulsion Preparation Step: The W1/O emulsion prepared in the step (1) is added with stirring to a mixed liquid of a water-soluble solvent (W2) and a mixed lipid component (F2) which forms the outer membrane of the liposome to prepare a W1/O/W2 emulsion. The inner portion of a single membrane composed of F2 is the W1/O emulsion and the outer portion thereof is a water phase (W2).

(3) The organic solvent contained in the emulsion prepared in the step (2) is eliminated using an evaporator to prepare a suspension of the liposome having an inner membrane of F1 and an outer membrane of F2.

(4) Compounds (various kinds of active components) to be encapsulated in the liposome are added with stirring to the suspension of the liposome prepared in the step (3) or to a water-soluble solvent in which a freeze-dried material of the liposome is re-dispersed. Via this step, a liposome with an inner membrane of F1 and an outer membrane of F2 in which specific compounds are encapsulated is obtained.

<Membrane Emulsion Method>

The membrane emulsion method also refers to a well-known method to prepare a liposome (for example, refer to Sosaku Ichikawa (2007): Novel method for preparing vesicles from a monodisperse emulsion aimed at controlling the size and improving the entrapment yield, Nihon Yakugakkai Nen-kai Yoshi-shu (Summary of the Annual Meeting of the Pharmaceutical Society of Japan), Vol. 127, No. 1, page 205). For example, via the following steps, a liposome having an inner and an outer membrane differing in membrane constituting component can be prepared.

(1) First Emulsion Preparation Step: A mixed liquid of a water-soluble solvent (W1) is permeated by applying pressure through a hydrophobic porous membrane having a predetermined pore diameter or through microchannels (slits) formed of a silicon substrate, and then statically extruded into an organic solvent (O) such as hexane, in which a mixed lipid component (F1) forming the inner membrane of a liposome is dissolved, to prepare a W1/O emulsion.

(2) Freeze-drying Step: The W1/O emulsion (water-phase droplets) prepared in the step (1) is freeze-dried using liquid nitrogen. Subsequently, under conditions maintaining the freeze-dried state of the droplets, the organic solvent (O) is replaced with an organic solvent such as hexane containing no lipid component. Thereafter, the organic solvent is evaporated and eliminated using an evaporator. Herein, the particle diameter of a liposome to be produced via such a freeze-drying step is allowed to be larger (about 1000-3000 nm) than that via any other production methods.

(3) Second Emulsion Preparation Step: The freeze-dried material prepared in the step (2) is hydrated in a water-soluble solvent (W2) in which a mixed lipid component (F2) forming the outer membrane of a liposome is dissolved. Via this step, a suspension of the liposome having an inner membrane of F1 and an outer membrane of F2 is prepared.

(4) Compounds (various kinds of active components) to be encapsulated in the liposome are added with stirring to the suspension of the liposome prepared in the step (3) or to a water-soluble solvent in which the freeze-dried material of the liposome is re-dispersed. Via this step, a liposome with an inner membrane of F1 and an outer membrane of F2 in which specific compounds are encapsulated is obtained.

<Supercritical Carbon Dioxide Method>

Via any of the conventional supercritical carbon dioxide methods (for example, refer to Japanese Patent Publication Open to Public Inspection No. 2005-162678), a liposome, in which the inner and outer membranes are formed of the same lipid component, is obtained. In contrast, in the present invention, no common organic solvent is used, but supercritical (including semi-supercritical) carbon dioxide is used as an oil phase in the case of the above microencapsulation method. Thereby, there can be prepared a liposome having an inner and an outer membrane differing in lipid component constitution and exhibiting improved characteristics such as the encapsulation rate, compared to a liposome prepared via any of the conventional microencapsulation methods. It is understood that the conventional supercritical carbon dioxide method is categorized, from the viewpoint of its liposome forming mechanism, into a backward-feed distillation method in the classification of the liposome production methods. In such a backward-feed distillation method, no liposome having the inner and outer membranes differing in lipid component constitution can be produced. And from the viewpoint of the necessity of elimination of solvents by distillation, a number of limitations exist with respect to the production method. A two-step emulsion method, being an improved supercritical carbon dioxide method, overcomes such limitations and makes it possible to prepare an SLV (single membrane) liposome exhibiting enhanced dispersion stability and relatively narrow particle size distribution.

The outline of the steps of such a production method is as follows.

(1) First Emulsion Preparation Step: Supercritical (including semi-supercritical) carbon dioxide, a water-soluble solvent (W1), and a mixed lipid component (F1) which forms the inner membrane of a liposome are stirred together to prepare a W1/CO2 emulsion. The inner portion of a single membrane composed of F1 is a water phase (W1) and the outer portion thereof is an oil phase (CO2).

(2) Second Emulsion Preparation Step: The W1/CO2 emulsion prepared in the step (1) is added with stirring to a mixed liquid of a water-soluble solvent (W2) and a mixed lipid component (F2) which forms the outer membrane of the liposome to prepare a W1/CO2/W2 emulsion. The inner portion of a single membrane composed of F2 is the W1/CO2 emulsion and the outer portion thereof is a water phase (W2).

(3) The organic solvent contained the emulsion prepared in the step (2) is eliminated using an evaporator to prepare a suspension of the liposome having an inner membrane of F1 and an outer membrane of F2.

(4) Compounds (various kinds of active components) to be encapsulated in the liposome are added with stirring to the suspension of the liposome prepared in the step (3) or to a water-soluble solvent in which a freeze-dried material of the liposome is re-dispersed. Via this step, a liposome with an inner membrane of F1 and an outer membrane of F2 in which specific compounds are encapsulated is obtained.

<Other Embodiments Differing from the Above Production Methods>

In any of the above embodiments including the microencapsulation method, the membrane emulsion method, and the supercritical carbon dioxide method, initially, an empty liposome is prepared, followed by being stirred with a compound to be encapsulated. Thereby, the compound is entrapped into the empty liposome.

Other than such a method, in each step (1) of the microencapsulation method, the membrane emulsion method, and the supercritical carbon dioxide method, compounds (various kinds of active components) to be encapsulated in a water-soluble solvent (W1) are dissolved, whereby the targeted liposome can also be prepared without use of the step (4).

<Other Steps>

In addition to the steps to prepare a liposome in any of the above methods, other steps may be provided if appropriate.

For example, after preparation of a liposome, there may be provided a step such that by allowing the liposome to further react with another compound, a specific functional group or chemical structure (for example, a site bonded with a ligand capable of imparting targeting properties to a predetermined cell via a linker or a site imparting hydrophilic properties such as a polyethylene glycol chain) is introduced into a lipid which forms the outer membrane.

Further, a filtration step may be provided if appropriate in which the particle diameter distribution of a liposome is adjusted to a desired range with elimination of impurities and sterilization. A liposome featuring a central particle diameter of about 100-300 nm can efficiently be prepared by allowing the liposome to pass, for example, through a static pressure extrusion apparatus equipped with a polycarbonate membrane or a cellulose membrane of a pore diameter of 0.1-0.4 µm as a filter. A liposome of such a size hardly blocks the capillaries and also has the advantage of passing through a gap generated in blood vessels near cancer tissues. As the above static pressure extrusion apparatus, listed are, for example, "EXTRUDER" (produced by Nichiyu Liposome Co.) and "LIPONIZER" (produced by Nomura Micro Science Co., Ltd.).

Further, it is desirable that after obtained, a suspension of a liposome is freeze-dried to allow the liposome to be in a suitable form for storage until use. Freeze-drying can be carried out using the same method or apparatus as in cases of the conventional liposome production. For example, via an indirect heating freeze-drying method, a refrigerant direct expansion method, a heating medium circulation method, a triple heat exchange method, or an overlapping freezing method, freeze-drying only needs to be performed under appropriate conditions (temperature: $-120$--$20°$ C.; pressure: 1-15 Pa; and duration: 16-26 hours).

EXAMPLES

Example 1

Production of a Liposome Contrast Medium Containing a Fatty Acid Ester only in the Inner Wall (1) Production of a Liposome by a Microencapsulation Method Using a 1-L pressure-resistant container equipped with a stirrer, 35 g of DPPC (produced by NOF Corp.), 5 g of DPPS (produced by NOF Corp.), and 2.5 g of methyl lignocerate were suspended in 200 g of water, and uniformly dispersed at a temperature of 20° C. at a revolution number of 470 rpm by addition of 280 g of hexane to obtain a W/O emulsion solution.

In a stainless steel container of 10 L separately provided, 6 kg of water, 100 ml of methanol, and 35 g of DPPC (produced by NOF Corp.) were placed and stirred at 370 rpm using a flat vane turbine blade (3 vanes) of a diameter of 8 cm, followed by addition of the W/O emulsion solution into the water over 30 minutes under a condition of atmospheric pressure and 20° C. to obtain a liposome solution. Subsequently, this liposome solution was subjected to depressurization using an evaporator on a water bath of 40°

C. under reduced pressure to eliminate the solvents. The thus-obtained aqueous solution was freeze-dried to obtain a powdery liposome.

(2) Production of a Liposome Contrast Medium Sixty-five g of "OMNIPARK 240" (a contrast medium which contains 517.7 mg of iohexol, produced by Konica Minolta Medical & Graphic, Inc.) was added to the powdery liposome obtained in (1) described above to carry out re-hydration and mixing. Thus, a liposome contrast medium was produced.

Comparative Example 1

Production of a Liposome Contrast Medium Containing a Fatty Acid Ester in the Inner Membrane and the Outer Membrane Constituting a Lipid Bimolecular Membrane A container was charged with 25 mg of methyl lignocerate having been heated (80° C.), followed by addition of 0.2 ml of ethanol to dissolve the methyl lignocerate in a hot bath of 80° C. Then, 6.5 g of "OMNIPARK 240" having been previously heated (50° C.) was added with mixing to the methyl lignocerate having been dissolved in the ethanol. Thereafter, 500 mg of dipalmitoyl phosphatidylcholine (DPPC) and 50 mg of dipalmitoyl phosphatidylserine (DPPS) were added as lipids to this resulting mixture, followed by being placed in a constant-temperature bath set at 50° C. to stir at 16000 revolutions/minute using an inserted homogenizer. The lipids having been mixed was left stand for 60 minutes to obtain a liposome contrast medium.

The determination results of the encapsulation rate and the average particle diameter of each of the liposome contrast media obtained in Example 1 and Comparative Example 1 are listed in Table 1. Herein, in EXAMPLES, encapsulation rates and average particle diameters were determined by the following methods.

<Evaluation of an Encapsulation Rate>

An obtained sample was placed in a small bottle of 20 ml and covered with a lid. The circumference of the lid was sealed with a sealing tape. Then, the sample was stored in a dark place under an ambience of 23° C. and 55% humidity for 60 minutes. Thereafter, this sample was dialyzed with an isotonic sodium chloride solution. After dialysis, a liposome was destroyed by adding ethanol to determine the amount of iodine compounds in the liposome via absorbance measurement. The ratio of the amount of the iodine compounds in the liposome to the amount of the total iodine compounds in the sample was designated as the encapsulation rate (% by mass).

<Evaluation of an Average Particle Diameter>

A particle diameter was determined in such a manner that a dispersion containing a liposome in which a water-soluble medical agent was encapsulated was measured using a dynamic light scattering particle size measurement instrument (Malvern HPPS, produced by Sysmex Corp.) under a condition of 25° C.

TABLE 1

|  | Comparative Example 1 | Example 1 |
|---|---|---|
| Encapsulation Rate | 32% | 52% |
| Average Particle Diameter | 171 nm | 252 nm |

Table 1 shows that of the lipid bimolecular membranes constituting the liposomes, the encapsulation rate of a contrast medium in the liposome containing a fatty acid only in the inner wall is increased to 52%, compared to the liposome containing a fatty acid in the inner and outer walls in equal amount.

Example 2

Production of a siRNA Encapsulated Liposome Containing a Cationic Lipid Only in the Inner Membrane of a Lipid Bimolecular Membrane 1) Production of a Liposome by a Microencapsulation Method Using a 1-L pressure-resistant container equipped with a stirrer, 30 g of DPPC (produced by NOF Corp.), 15 g of cholesterol (produced by NOF Corp.), and 15 g of DOTMA (N-(2,3-(dioleyloxy)propyl-N,N,N-trimethylammonium chloride) were suspended in 200 g of water, and uniformly dispersed at a temperature of 20° C. at a revolution number of 470 rpm by addition of 280 g of hexane to obtain a W/O emulsion solution.

In a stainless steel container of 10 L separately provided, 6 kg of water, 100 ml of methanol, and 35 g of DPPC (produced by NOF Corp.) were placed and stirred at 370 rpm using a flat vane turbine blade (3 vanes) of a diameter of 8 cm, followed by addition of the W/O emulsion solution into the water over 30 minutes under a condition of atmospheric pressure and 20° C. to obtain a liposome solution. Subsequently, this liposome solution was subjected to depressurization using an evaporator on a water bath of 40° C. under reduced pressure to eliminate the solvents. The thus-obtained aqueous solution was freeze-dried to obtain a powdery liposome.

(2) Production of an siRNA Encapsulated Liposome Eighty mg of the powdery liposome obtained in (1) described above was hydrated with 5 ml of an aqueous solution of an siRNA (1 mg, trade name "siRNA-Luc+", produced by Dharmacon, Inc.) with mixing to produce an siRNA encapsulated liposome.

Comparative Example 2

Production of a siRNA Encapsulated Liposome Containing a Cationic Lipid in the Inner and Outer Membranes Constituting a Lipid Bimolecular Membrane in Equal Amount Based on the method described in Japanese Translation of PCT International Application Publication No. 2005-538967, there were prepared 5 ml of a water-ethanol (1:1) solution dissolving a total amount of 50 mg of membrane constituting lipid components composed of DSPC:cholesterol:PEG-DSG:DOTMA=20:45:10:25 and a solution dissolving 5 mg of an siRNA (produced by Dharmacon, Inc.). Then, both aqueous solutions were introduced into a peristaltic pump mixer at the same rate (60 ml/minute) for mixing.

The determination results of the encapsulation rate and the average particle diameter of each of the siRNA encapsulated liposomes obtained in Example 2 and Comparative Example 2 are listed in Table 2. The results show that since zeta potential indicating the surface potential of the outer membrane of the lipid bimolecular membrane approaches zero, only a small amount of the cationic lipid is present in the outer membrane; and of the lipid bimolecular membranes constituting the liposomes, when the cationic lipid is present more in the inner membrane than in the outer membrane, the encapsulation rate of the siRNA is increased to 76%.

TABLE 2

|  | Example 2 | Comparative Example 2 |
|---|---|---|
| Zeta Potential | +0.9 mV | +10.3 mV |
| Encapsulation Rate | 76% | 58% |
| Average Particle Diameter | 272 nm | 191 nm |

Example 3

Production of an siRNA Encapsulated Liposome Containing a Cationic Pullulan Only in the Inner Membrane of a Lipid Bimolecular Membrane (1) Production of a Liposome by Microencapsulation Method Using a 1-L pressure-resistant container equipped with a stirrer, 30 g of DPPC (produced by NOF Corp.), 10 g of cholesterol (produced by NOF Corp.), and 5 g of a cationic pullulan were suspended in 200 g of water, and uniformly dispersed at a temperature of 20° C. at a revolution number of 470 rpm by addition of 280 g of hexane to obtain a W/O emulsion solution.

In a stainless steel container of 10 L separately provided, 6 kg of water, 100 ml of methanol, and 35 g of DPPC (produced by NOF Corp.) were placed and stirred at 370 rpm using a flat vane turbine blade (3 vanes) of a diameter of 8 cm, followed by addition of the W/O emulsion solution into the water over 30 minutes under a condition of atmospheric pressure and 20° C. to obtain a liposome solution. Subsequently, this liposome solution was subjected to depressurization using an evaporator on a water bath of 40° C. under reduced pressure to eliminate the solvents. The thus-obtained aqueous solution was freeze-dried to obtain a powdery liposome.

(2) Production of an siRNA Encapsulated Liposome

Eighty mg of the powdery liposome obtained in (1) described above was hydrated with 5 ml of an aqueous solution of an siRNA (1 mg, trade name "siRNA-Luc+", produced by Dharmacon, Inc.) with mixing to produce an siRNA encapsulated liposome.

Comparative Example 3

Production of an siRNA Encapsulated Liposome Containing a Cationic Pullulan in the Inner and Outer Membranes Constituting a Lipid Bimolecular Membrane in Equal Amount Using a 1-L pressure-resistant container equipped with a stirrer, 30 g of DPPC (produced by NOF Corp.), 10 g of cholesterol (produced by NOF Corp.), and 5 g of a cationic pullulan (prepared by the method based on paragraph [0018] of Japanese Patent Publication Open to Public Inspection No. 2006-028061) were suspended in 200 g of water, and uniformly dispersed at a temperature of 20° C. at a revolution number of 470 rpm by addition of 280 g of hexane to obtain a W/O emulsion solution.

In a stainless steel container of 10 L separately provided, 6 kg of water, 100 ml of methanol, 35 g of DPPC (produced by NOF Corp.), 10 g of cholesterol (produced by NOF Corp.), and 5 g of the cationic pullulan were placed and stirred at 370 rpm using a flat vane turbine blade (3 vanes) of a diameter of 8 cm, followed by addition of the W/O emulsion solution into the water over 30 minutes under a condition of atmospheric pressure and 20° C. to obtain a liposome solution. Subsequently, this liposome solution was subjected to depressurization using an evaporator on a water bath of 40° C. under reduced pressure to eliminate the solvents. The thus-obtained aqueous solution was freeze-dried to obtain a powdery liposome.

(2) Production of an siRNA Encapsulated Liposome

Eighty mg of the powdery liposome obtained in (1) described above was hydrated with 5 ml of an aqueous solution of an siRNA (1 mg, trade name "siRNA-Luc+", produced by Dharmacon, Inc.) with mixing to produce an siRNA encapsulated liposome.

The determination results of the encapsulation rate and the average particle diameter of each of the siRNA encapsulated liposomes obtained in Example 3 and Comparative Example 3 are listed in Table 3.

TABLE 3

|  | Example 3 | Comparative Example 3 |
|---|---|---|
| Zeta Potential | +1.1 mV | +17.3 mV |
| Encapsulation Rate | 71% | 66% |
| Average Particle Diameter | 280 nm | 141 nm |
| Over-time Stability | No aggregation observed after 2 weeks | Aggregation visually observed after 2 weeks |

The determination results of the encapsulation rate and the average particle diameter of each of the siRNA encapsulated liposomes obtained in Example 3 and Comparative Example 3 are listed in Table 3. The results show that since zeta potential indicating the surface potential of the outer membrane of the lipid bimolecular membrane of Example 3 approaches zero, compared to Comparative Example 3, only a small amount of the cationic lipid is present in the outer membrane; and of the lipid bimolecular membranes constituting the liposomes, when the cationic lipid is present more in the inner membrane than in the outer membrane, the encapsulation rate of the siRNA is increased to 71%.

Example 4

Production of an siRNA Encapsulated Liposome Containing a Cationic Lipid Only in the Inner Wall and a Transferrin-Modified PEG Lipid Only in the Outer Wall (1) Production of a Liposome by a Microencapsulation Method Using a 1-L pressure-resistant container equipped with a stirrer, 30 g of DPPC (produced by NOF Corp.), 15 g of cholesterol (produced by NOF Corp.), and 15 g of DOTMA (N-(2,3-(dioleyloxy)propyl-N,N,N-trimethyl-ammonium chloride) were suspended in 200 g of water, and uniformly dispersed at a temperature of 20° C. at a revolution number of 470 rpm by addition of 280 g of hexane to obtain a W/O emulsion solution.

In a stainless steel container of 10 L separately provided, 6 kg of water, 100 ml of methanol, 35 g of DPPC (produced by NOF Corp.), 1.5 g of "DSPE (distearoyl phosphatidylethanolamine)-PEG-OMe", and 0.2 g of "DSPE-PEG-COOH" were placed and stirred at 370 rpm using a flat vane turbine blade (3 vanes) of a diameter of 8 cm, followed by addition of the W/O emulsion solution into the water over 30 minutes under a condition of atmospheric pressure and 20° C. to obtain a liposome solution.

(2) Introduction of Transferrin

Fifty mg of 1-ethyl-3-(3-dimethylamino-propyl)carbodiimide hydrochloric acid and 100 mg of N-hydroxysulfosuccinimide were added to the liposome solution obtained in (1) described above, followed by being left stand at room temperature for 10 minutes. Then, 200 mg of transferrin was added and the resulting mixture was stirred at room temperature for 3 hours. Centrifugation was carried out at 200,000 Xg for 30 minutes and the resulting precipitates were re-suspended in a 9% sucrose solution. Subsequently, iron citrate-sodium citrate was added, followed by being stirred at room temperature for 15 minutes. The resulting product was centrifuged at 200,000 Xg for 30 minutes and then the resulting precipitates were re-suspended in the 9% sucrose solution.

The obtained liposome solution was subjected to depressurization using an evaporator on a water bath of 40° C. under reduced pressure to eliminate the solvents. The thus-obtained aqueous solution was freeze-dried to obtain a powdery liposome. Incidentally, a larger number of transferrin receptors are present on the surface of tumor cells than normal cells. Therefore, such transferrin introduced as described above contributes to targeting at such tumor cells of a liposome.

(3) Production of an siRNA Encapsulated Liposome

Eighty mg of the powdery liposome obtained in (2) described above was hydrated with 5 ml of an aqueous solution of an siRNA (1 mg, trade name "siRNA-Luc+", produced by Dharmacon, Inc.) with mixing to produce an siRNA encapsulated liposome.

Example 5

Production of an siRNA Encapsulated Liposome Containing a Cationic Lipid Employing Supercritical Carbon Dioxide as an Oil Phase Only in the Inner Wall and a Transferrin-Modified PEG Lipid Only in the Outer Wall (1) Production of a Liposome by an Improved Supercritical Carbon Dioxide Method Using a 200-ml pressure-resistant container equipped with a stirrer, 0.51 g of DPPC (produced by NOF Corp.), 0.18 g of cholesterol (produced by NOF Corp.), and 0.04 g of DOTMA (N-(2,3-(dioleyloxy)propyl-N, N,N-trimethylammonium chloride) were dissolved in 14.3 g of ethanol, followed by being sealed. Then, 85 g of supercritical carbon dioxide was introduced over 5 minutes and stirring was carried out at a temperature of 60° C. under a pressurized state of 19 MPa. The number of revolutions for the stirring was 50 rpm. Using HPLC, 5 ml of water was introduced into the container at a feeding rate of 1.6 ml/minute for uniform dispersion to obtain a W/O emulsion solution.

Using a pressure-resistant container of 500 ml equipped with a stirrer separately provided, 0.25 g of DPPC (produced by NOF Corp.), 0.10 g of cholesterol (produced by NOF Corp.), 0.02 g of "DSPE-PEG-OMe", and 0.008 g of "DSPE-PEG-COOH" were dissolved in 14.3 ml of ethanol, followed by being sealed after further addition of 445 g of water. An appropriate amount of supercritical carbon dioxide was introduced to generate a pressurized state of 8 MPa at a temperature of 60° C. Then, the above W/O emulsion solution was introduced into the pressure-resistant container of 500 ml equipped with a stirrer at a feeding rate of 10 ml using HPCL while stirring at a revolution number of 59 rpm. The W/O emulsion solution in a pressure-resistant container of 200 ml equipped with a stirrer was entirely fed over 35 minutes and thereafter depressurization was carried out for discharge of carbon dioxide to obtain a liposome solution.

(2) Introduction of Transferrin

Fifty mg of 1-ethyl-3-(3-dimethylamino-propyl)carbodiimide hydrochloric acid and 100 mg of N-hydroxysulfosuccinimide were added to the liposome solution obtained in (1) described above, followed by being left stand at room temperature for 10 minutes. Then, 200 mg of transferrin was added and the resulting mixture was stirred at room temperature for 3 hours. Centrifugation was carried out at 200,000 Xg for 30 minutes and the resulting precipitates were re-suspended in a 9% sucrose solution. Subsequently, iron citrate-sodium citrate was added, followed by being stirred at room temperature for 15 minutes. The resulting product was centrifuged at 200,000 Xg for 30 minutes and then the resulting precipitates were re-suspended in the 9% sucrose solution.

The obtained liposome solution was subjected to depressurization using an evaporator on a water bath of 40° C. under reduced pressure to eliminate the solvents. The thus-obtained aqueous solution was freeze-dried to obtain a powdery liposome.

(3) Production of an siRNA Encapsulated Liposome

Eighty mg of the powdery liposome obtained in (2) described above was hydrated with mixing using 5 ml of an aqueous solution of an siRNA (1 mg, trade name "siRNA-Luc+", produced by Dharmacon, Inc.) inhibiting expression of a firefly luciferase gene to produce an siRNA encapsulated liposome.

Comparison Test of RNAi Effects

A human liver cancer cell (HuH-7 cell) was sowed in a 24-well cell culture plate made of polystyrene (produced by Falcon Co.) at 5×10⁴ cells/well and cultured for 24 hours. Thereafter, using "LipofectAMINE" (1.22 µl/well, produced by Invitrogen Corp.), reporter genes of a firefly luciferase plasmid DNA (0.084 µg/well, "pGL-3" produced by Promega KK) and a Renilla luciferase plasmid DNA (0.75 µg/well, "pRL-TK" produced by Promega KK) were transfected into the cells in OptiMEM (produced by Invitrogen Corp.).

Subsequently, a solution (siRNA concentration: 100 mM), in which each of the liposomes obtained in Example 3, Comparative Example 3, Example 4, and Example 5 was re-hydrated, was added to allow the solution to be brought into contact with the cells in the presence of serum of 10% for 24 hours.

Thereafter, the cells were recovered and the expression amounts of the above reporter genes were determined using "Dual Luciferase Reporter Assay System" (produced by Promega KK). Then, RNAi effects were compared based on the values of the expression amount of the firefly luciferase/the expression amount of the Renilla luciferase ([pGL]/[pRL]). The results are listed in Table 4.

TABLE 4

|  | [pGL]/[pRL] |
| --- | --- |
| Control | 100% |
| siRNA only | 82% |
| Example 3 | 65% |
| Example 4 | 55% |
| Example 5 | 49% |
| Comparative Example 3 | 70% |

The evaluation experiments using the above cultured cells showed that of reporter genes released from 2 types of plasmids activated by cultured cells, that is, the firefly luciferase gene and the Renilla luciferase gene, the expression amount of the former was dominantly decreased; and this fact was shown by the comparison of the expression amounts ([pGL] and [pRL]) of proteins which were products from the genes. And the magnitude of the level of such a dominant decrease of the expression amount of a firefly luciferase gene depends on the absolute amount of an siRNA which inhibits expression of the firefly luciferase gene. Namely, the larger the value (%) of [pGL]/[pRL] is, the larger the expression amount of the firefly luciferase gene is, which indicates that the absolute amount of the siRNA is small (the encapsulation rate of the siRNA is small). In contrast, the smaller the value (%) of [pGL]/[pRL] is, the smaller the expression amount of the firefly luciferase gene is, which indicates that the absolute amount of the siRNA is large (the encapsulation rate of the siRNA is large). Consequently, the results of Table 4 are understood as follows: when only the siRNA was allowed to be in contact with cultured cells, the decrease of the gene expression amount was only (100%−82%=18%) due to the decrease of the decomposition/absolute amount resulting from well-known instability of the siRNA; and in contrast, in Examples 4 and 5, sine the siRNA stably existed in the liposomes, the decrease of the gene expression amount became larger. Further, it is understood that in Example 3, compared to Comparative Example 3, the absolute amount of the siRNA in the liposome was relatively large, whereby the decrease of the gene expression amount became larger.

The invention claimed is:

1. A method for producing a liposome comprising a lipid bimolecular membrane composed of:
    an inner membrane comprising a first component (F1) which comprises a cationic pullulan, one or more functional lipids selected from the group consisting of cationic lipid, an anionic phospholipid, and an aliphatic acid ester, or a combination thereof; and
    an outer membrane comprising a second component (F2) which comprises a functional lipid, wherein the functional lipid is a phospholipid,
    the method comprising the steps of (1)-(3);
    (1) mixing:
        supercritical or semi-supercritical carbon dioxide or an organic solvent (o);
        a water-soluble solvent (W1); and
        the first component (F1) which forms an inner membrane of the liposome
        so as to prepare a W1/CO2 emulsion or a W1/O emulsion (a first emulsion preparation step);
    (2) adding the W1/CO2 emulsion or the W1/O emulsion prepared in the step (1) to a mixture of a water-soluble solvent (W2) and the second component (F2) with stirring so as to prepare a W1/CO2/W2 emulsion or a W1/O/W2 emulsion (a second emulsion preparation step);
    (3) eliminating the solvents contained in the W1/CO2/W2 emulsion or the W1/O/W2 emulsion prepared in the step (2) so as to prepare a suspension of the liposome comprising the inner membrane composed of the first component F1 and the outer membrane composed of the second component F2;
    wherein an amount of at least one (F11) of the cationic pullulan or the functional lipids contained in F1 is larger than an amount of the at least one (F11) in F2.

2. The method according to claim 1, further comprising (4) adding a compound to be encapsulated in the liposome to the suspension of the liposome prepared in the step (3), or to a water-soluble solvent in which a freeze-dried material of the suspension of the liposome prepared in the step (3) is re-dispersed.

3. The method according to claim 2,
    wherein step (1) comprises mixing supercritical or semi-supercritical carbon dioxide, W1 and F1.

4. The method according to claim 1,
    wherein at least one of the functional lipids is a compound which chemically interacts with a compound to be encapsulated in the liposome.

5. The method according to claim 2,
    wherein the compound to be encapsulated in the liposome is a nucleic acid.

6. The method according to claim 5,
    wherein the anionic compound is a siRNA which has an anticancer activity.

7. The method according to claim 2,
    wherein the compound to be encapsulated in the liposome is a contrast medium.

8. The method according to claim 2, wherein at least one of the functional lipids is a compound which chemically interacts with a compound to be encapsulated in the liposome.

9. The method according to claim 3, wherein at least one of the functional lipids is a compound which chemically interacts with a compound to be encapsulated in the liposome.

10. The method according to claim 3, wherein the compound to be encapsulated in the liposome is a nucleic acid.

11. The method according to claim 4, wherein the compound to be encapsulated in the liposome is a nucleic acid.

12. The method according to claim 3, wherein the compound to be encapsulated in the liposome is a contrast medium.

13. The method according to claim 4, wherein the compound to be encapsulated in the liposome is a contrast medium.

14. The method according to claim 1, wherein the cationic lipid is selected from the group consisting of 1,2-dioleoyloxy-3-(trimethylamrnonium)propane, N,N-dioctadecylamidoglycylspermine, dimethyloctadecylammonium bromide, N-[1-(2,3-dioleyloxyl)propyl]-N,N,N-trimethylammonium chloride, 2,3-dioleyloxy-N-[2(spermine-carboxamido)ethyl]-N,N-dimethyl-1-propaneaminiumtrifluoroacetate, N-[1-(2,3-dimyristyloxy)propyl]-N,N-dimethyl-N-(2-hydroxyethyl)ammonium bromide, an ester of dipalmitoylphosphatidic acid with hydroxyethylenediamine, and an ester of distearoylphosphatidic acid and hydroxyethylenediamine.

* * * * *